United States Patent
Chen et al.

(10) Patent No.: US 11,291,387 B2
(45) Date of Patent: Apr. 5, 2022

(54) SYSTEM FOR RECOGNIZING ABNORMAL ACTIVITY OF HUMAN BODY USING WEARABLE ELECTRONIC DEVICE AND MIXED REALITY TECHNOLOGY

(71) Applicant: WE JUMP INTELLIGENT PERCEPTION CO., LTD., Taipei (TW)

(72) Inventors: Ching-Han Chen, Taipei (TW); Min-Ying Lin, Taipei (TW); Po-Shih Chiang, Taipei (TW)

(73) Assignee: We Jump Intelligent Perception Co., Ltd., Taipei (TW)

(*) Notice: Subject to any disclaimer, the term of this patent is extended or adjusted under 35 U.S.C. 154(b) by 71 days.

(21) Appl. No.: 16/835,561

(22) Filed: Mar. 31, 2020

(65) Prior Publication Data
US 2021/0298644 A1    Sep. 30, 2021

(51) Int. Cl.
| | |
|---|---|
| *A61B 5/11* | (2006.01) |
| *A61B 5/00* | (2006.01) |
| *G06T 19/00* | (2011.01) |
| *G06F 3/01* | (2006.01) |
| *G02B 27/01* | (2006.01) |

(52) U.S. Cl.
CPC .......... *A61B 5/1118* (2013.01); *A61B 5/6814* (2013.01); *A61B 5/6824* (2013.01); *G02B 27/017* (2013.01); *G06F 3/012* (2013.01); *G06F 3/014* (2013.01); *G06T 19/006* (2013.01)

(58) Field of Classification Search
CPC ... A61B 5/1118; A61B 5/6824; A61B 5/6814; G06F 3/012; G06F 3/014; G06T 19/006; G02B 27/017
See application file for complete search history.

(56) References Cited

FOREIGN PATENT DOCUMENTS

| | | | | |
|---|---|---|---|---|
| CN | 107273728 A | * | 10/2017 | |
| CN | 109767600 A | * | 5/2019 | |
| WO | WO-2019104172 A1 | * | 5/2019 | ........... A61B 5/0006 |
| WO | WO-2019244125 A2 | * | 12/2019 | ......... G08B 21/0461 |

* cited by examiner

*Primary Examiner* — Jeffery A Brier
(74) *Attorney, Agent, or Firm* — Karin L. Williams; Alan D. Kamrath; Mayer & Williams PC (57) ABSTRACT

A system for recognizing abnormal activity of human body using wearable electronic device and mixed reality technology, includes a first wearable electronic device, a plurality of second wearable electronic devices, at least one camera, and a judgement module. The system is suitable to be applied in any type of work environment, so as to monitor and determine whether a user (i.e., an operator or an employee) exhibits abnormal activities by referring a document of standard operating procedures (SOP), an operating manual and a document of safety operation standard (SOS), to reduce a rate of user mishandling, thereby achieving the enhancement of work efficiency and productivity.

17 Claims, 7 Drawing Sheets

SYSTEM FOR RECOGNIZING ABNORMAL ACTIVITY OF HUMAN BODY USING WEARABLE ELECTRONIC DEVICE AND MIXED REALITY TECHNOLOGY

BACKGROUND OF THE INVENTION

1. Field of the Invention

The present invention relates to the technology field of wearable electronic device application, and more particularly to a system for recognizing abnormal activity of human body using wearable electronic device and mixed reality technology.

2. Description of the Prior Art

It is well known that a new employee of a company is commonly required to receive a standard employee training. Moreover, in many instances, there needs to be a qualification, such as a test, following the training so as to ensure that the new employee has attained the knowledge and skills associated with the new proficiency. Therefore, during the standard employee training, the employee trainer would provide document of standard operating procedures (SOP) and operating manual to the new employee receiving training, and subsequently providing a standard job orientation to the new employee according to training steps recorded in a standard teaching handbook. After completing the standard employee training, the new employee is able to perform his job and/or operate a machine by repeatedly practicing and following the prescribed order of the SOP document and the operating manual.

However, in spite of the fact that an employee has the skills to perform his job and/or operate a machine responsibly, as well as has fully understood the contents of the SOP document and the operating manual, an unexpected situation that suddenly occurs in a work environment and/or potential risks of the work environment, may still lead the employee to show mishandling when operating a specific machine. More seriously, the suddenly-occurring unexpected situation and/or the potential risks of the work environment may eventually result in the occurrence of workplace incident. In view of that, human-factors engineering is hence developed and implemented into the management on improving and adapting technology, equipment and work environments to complement employee behavior and capabilities. It is a pity that human-factors engineering has been found to show application limits, thereby failing to be properly implemented into any kinds of work environment. For example, when designing a production machine, human-factors engineering demands a mechanical engineer to develop the production machine to have a human-machine system, so as to make an operator show extremely-less mishandling when operating the production machine, thereby achieving the enhancement of work efficiency and productivity. However, in reality, it is very difficult and even impossible to develop or redesign each of production-relative devices to be or have a human-machine system.

From the above descriptions, it is understood that there is a need for developing a novel and different system, so as to apply this newly-developed system to any kind of work environment for effectively reducing the rate of an operator's mishandling, thereby achieving an enhancement of work efficiency and productivity. In view of that, inventors of the present application have made great efforts to perform inventive research and eventually provided a system for recognizing abnormal activity of the human body using a wearable electronic device and mixed reality technology.

SUMMARY OF THE INVENTION

The primary objective of the present invention is to disclose a system for recognizing abnormal activity of the human body using a wearable electronic device and mixed reality technology, including a first wearable electronic device, a plurality of second wearable electronic devices, at least one camera module, and a judgment module. This novel system is suitable for application in any type of work environment, so as to monitor and determine whether a user (i.e., an operator or an employee) exhibits abnormal activities by referring a document of standard operating procedures (SOP), an operating manual and a document of safety operation standard (SOS), such that it is facilitated to reduce a rate of the user's mishandling from happening, thereby achieving an enhancement of work efficiency and productivity.

Moreover, under the application of the system for recognizing abnormal activity of human body using wearable electronic device and mixed reality technology, a staff of a back-end management system is able to immediately monitor each of the operators by using the system, thereby confirming each of the operators is performing his job and/or machine operation responsibly, and is meeting the requirements of the SOP document, the operating manual and the SOS document. On the other hand, this system is also provided with a body pose forecasting function, such that the system of the present invention would transmit a warning signal to the back-end management system in case of a next body pose of the operator being forecasted to be an abnormal human activity. As a result, the staff of the back-end management system is able to inform the operator to fix his body pose in advance, thereby effectively avoiding the workplace incident from occurring due to the operator's mishandling.

In order to achieve the primary objective of the present invention, the inventor of the present invention provides an embodiment for the system for recognizing abnormal activity of human body, comprising:

a first wearable electronic device, configured to be worn on a head portion of a user, and having an image capturing unit and a head motion sensor unit, wherein the image capturing unit is used for capturing a first image including at least one object and a work environment, and the head motion sensor unit being used for achieving a head motion detection of the head portion;

a plurality of second wearable electronic devices, configured to be worn on two wrist portions of the user, and having a wrist motion sensor unit for achieving a wrist motion detection of each of the two wrist portions;

at least one camera, configured to capture a second image including the user, the at least one object and the work environment, and having a body pose forecasting unit for generating a body pose forecast data according to at least one body pose feature that is extracted from the second image;

a judgment module, being coupled to the first wearable electronic device, the plurality of wearable electronic devices and the camera, and comprising:

a data fusion unit, configured to receive a first object recognition data, a first circumstance recognition data including a head activity recognition data and a work environment recognition data that are transmitted from the first wearable electronic device, a wrist activity recognition data that is transmitted from second wearable electronic devices, and a second object recognition data, a second circumstance recognition data and the body pose forecast data that are transmitted from the camera, thereby generating a fusion data; and a judgment unit, being coupled to the data fusion unit, so as to determine whether the user is in an event of abnormal body activity or not, under referring the fusion data that is transmitted from the data fusion unit and at least one reference data.

In one embodiment, the forgoing first wearable electronic device is selected from the group consisting of mixed reality headset and smart glasses.

In one embodiment, the forgoing second wearable electronic device 12 is selected from the group consisting of smart wristband and smart watch.

In one embodiment, the judgment module further includes a storage unit for storing the reference data that includes a document of standard operating procedures (SOP), an operating manual and a document of safety operation standard (SOS).

In one embodiment, the head motion sensor unit and the wrist motion sensor unit both include at least one inertial sensor.

In one embodiment, the judgment module is a data processing device that is selected from the group consisting of central control system, industrial computer, server computer, desk computer, laptop computer, tablet PC, and smart phone.

In one embodiment, the head motion detection is selected from the group consisting of rotation angle detection, rotation frequency detection, tilt angle detection, position detection, and a combination of the forgoing two or more detections.

In one embodiment, the wrist motion detection is selected from the group consisting of rotation angle detection, rotation frequency detection, tilt angle detection, position detection, and a combination of the forgoing two or more detections.

In one embodiment, the forgoing system for recognizing abnormal activity of human body proposed by the present further includes a third wearable electronic device that is coupled to the judgment module, and configured to be worn on a hand portion of the user, and including a hand motion sensor unit for achieving a hand motion detection of the hand portion of the user; and a hand activity recognizing unit, being configured for generating a hand activity recognition data for the judgment module by applying a hand activity recognizing process to a hand motion sensing data that is transmitted from the hand motion sensor unit.

In one embodiment, the hand motion detection is selected from the group consisting of rotation angle detection, rotation frequency detection, tilt angle detection, position detection, detection of first clenching, detection of hand opening, finger activity detection, and a combination of the forgoing two or more detections.

In one embodiment, the judgment module of the forgoing system for recognizing abnormal activity of human body proposed by the present further includes a data synchronization unit, being coupled to the first wearable electronic device, the plurality of second wearable electronic devices, the camera, and the third wearable electronic device, so as to transmit a data synchronization signal to the first wearable electronic device, the plurality of second wearable electronic devices, the camera, and the third wearable electronic device, such that the data fusion unit simultaneously receives the first object recognition data, the first circumstance recognition data, the head activity recognition data, the wrist activity recognition data, the second object recognition data, the second circumstance recognition data, the body pose forecast data, and the hand activity recognition data.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

To more clearly describe a system for recognizing abnormal activity of a human body using a wearable electronic device and mixed reality technology disclosed by the present invention, embodiments of the present invention will be described in detail with reference to the attached drawings hereinafter.

Figure 1:
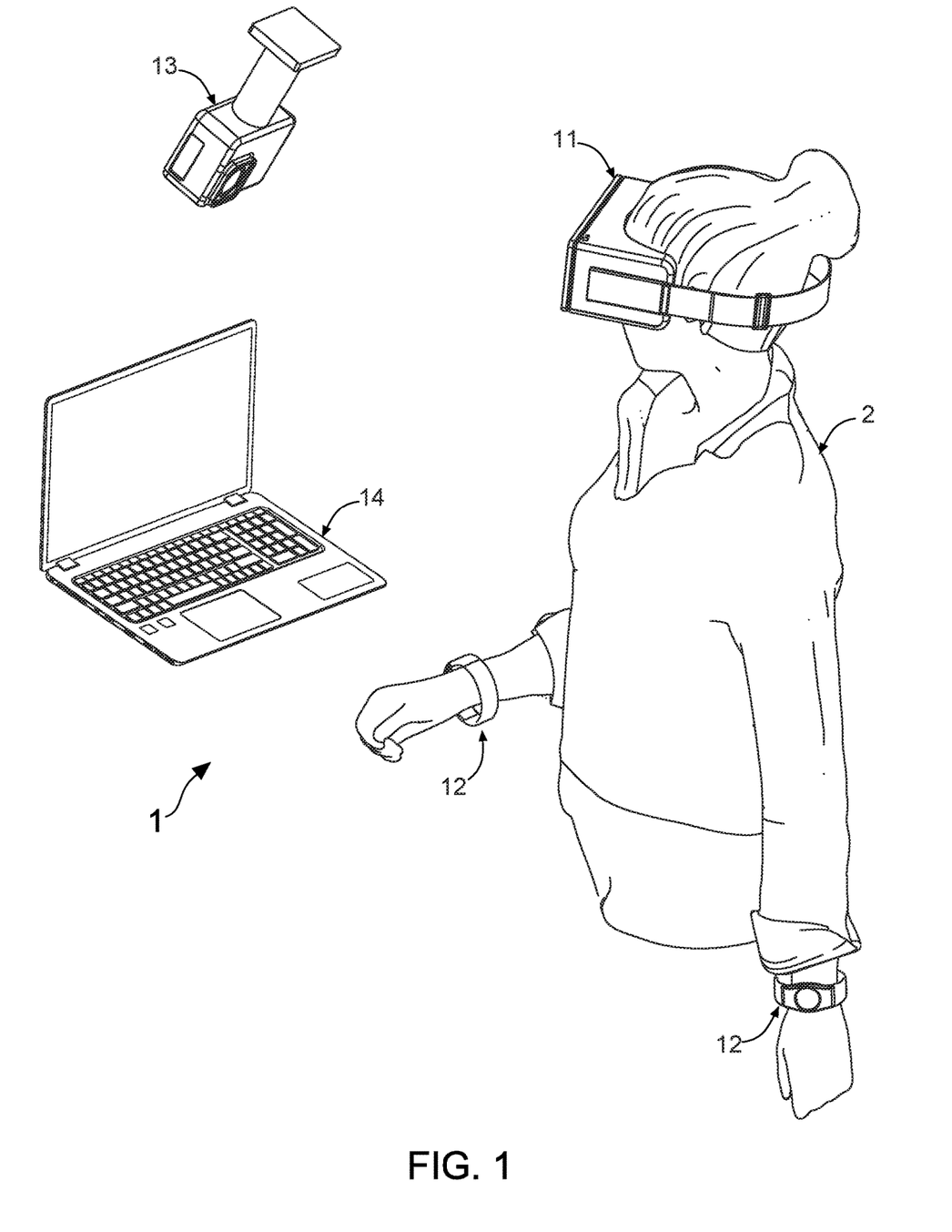
FIG. 1 shows a first diagram for describing a system for recognizing abnormal activity of human body using wearable electronic device and mixed reality technology according to the present invention.

With reference to FIG. 1, there is shown a first diagram for describing a system for recognizing abnormal activity of human body using wearable electronic device and mixed reality technology according to the present invention. The present invention discloses a system 1 for recognizing abnormal activity of human body of a user 2, and mainly includes a first wearable electronic device 11, a plurality of second wearable electronic devices 12, at least one camera 13, and a judgment module 14. Particularly, this novel system 1 is suitable for applying in any kinds of work environment, so as to monitor and determine whether the user 2 (i.e., an operator or an employee) exhibits abnormal activities by referring a document of standard operating procedures (SOP), an operating manual and a document of safety operation standard (SOS), such that it is facilitated to reduce a happening rate of the user's mishandling, thereby achieving the enhancement of work efficiency and productivity.

Figure 2:
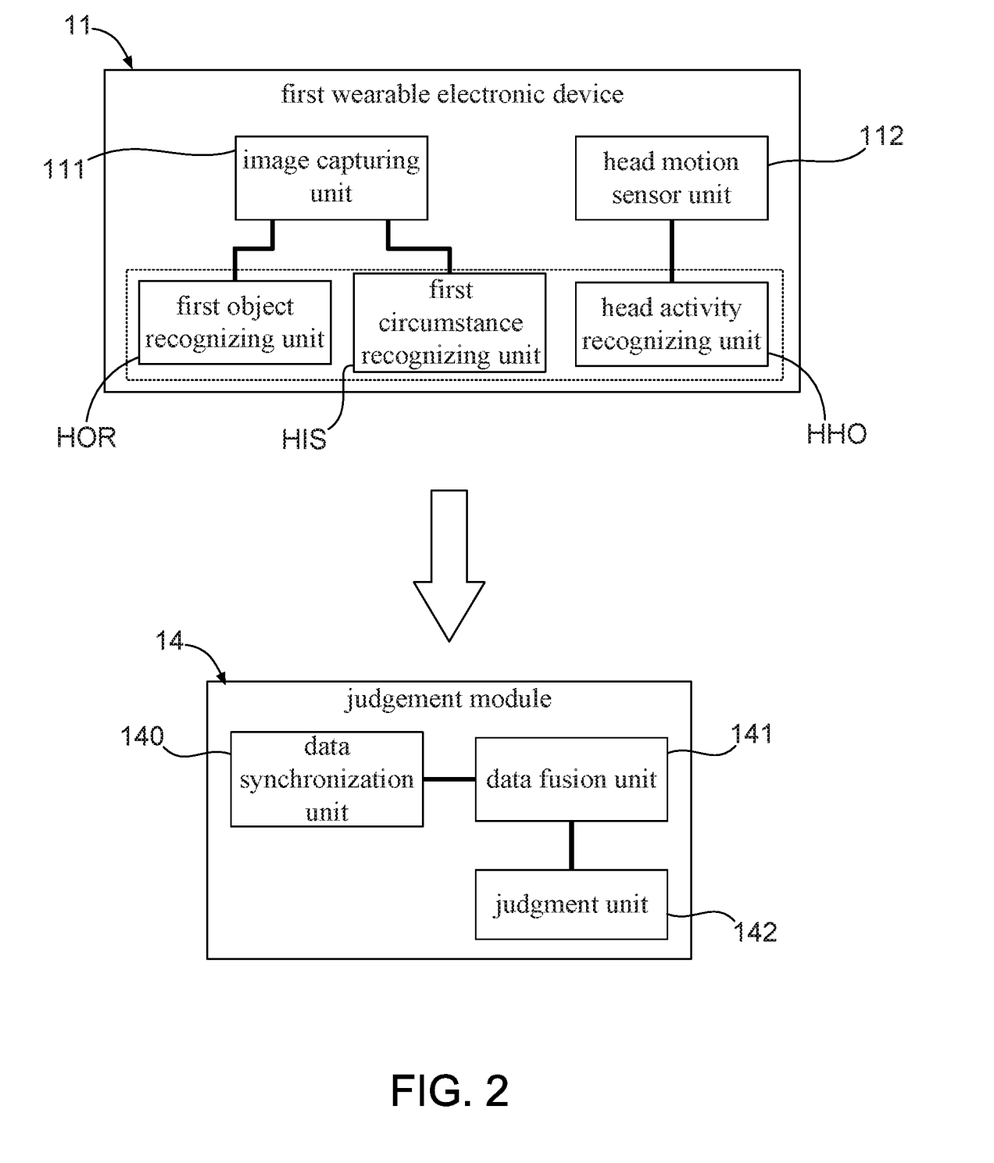
FIG. 2 shows a block diagram of a first wearable electronic device and a judgment module of the system for recognizing abnormal activity of human body.
Figure 3:
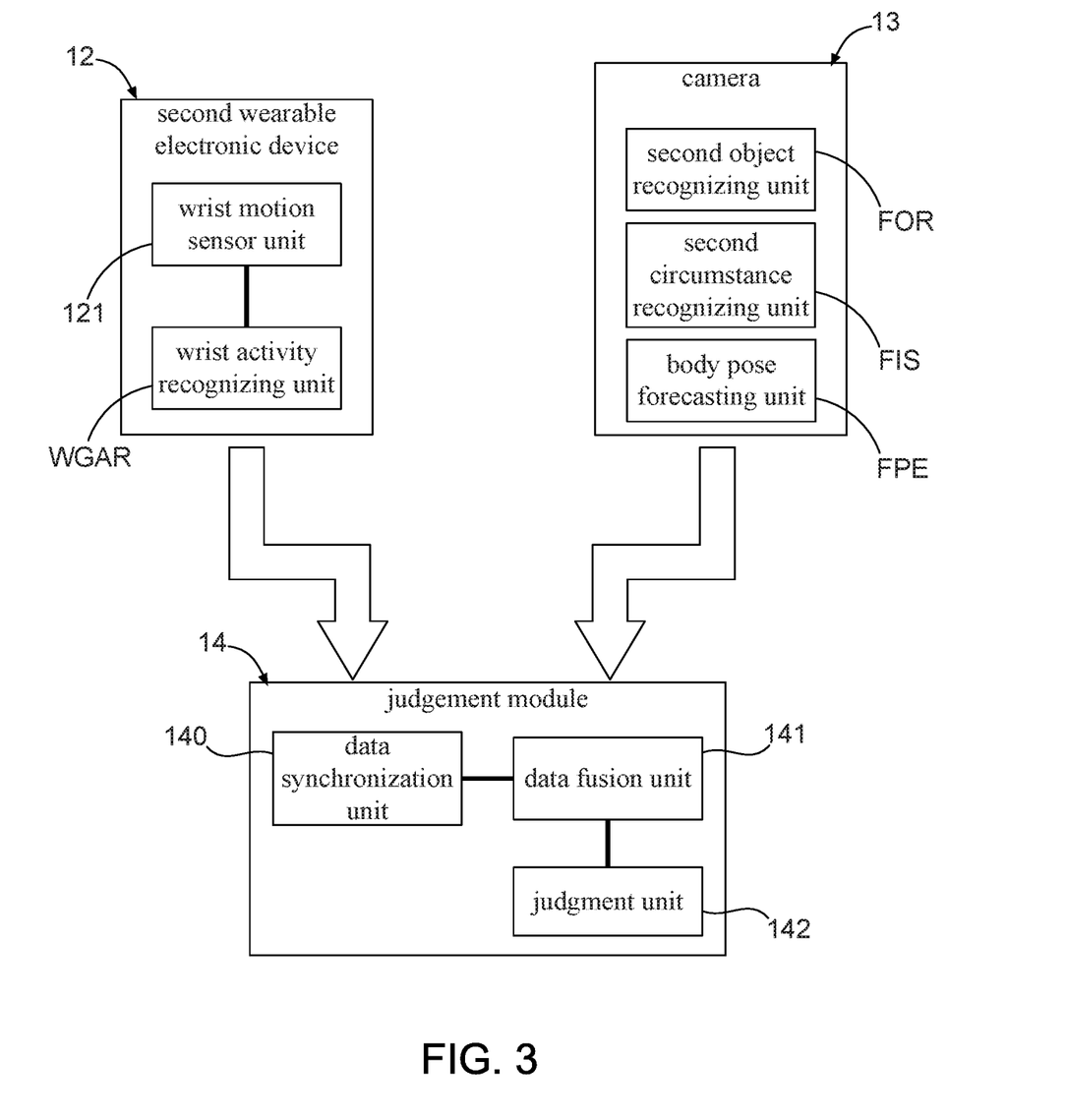
FIG. 3 shows a block diagram of a second wearable electronic device and the judgment module of the system for recognizing abnormal activity of human body.

FIG. 2 shows a block diagram of the first wearable electronic device 11 and the judgment module 14 of the system 1 for recognizing abnormal activity of human body. Moreover, FIG. 3 depicts a block diagram of the second wearable electronic device 12 and the judgment module 14 of the system 1 for recognizing abnormal activity of human body. From FIG. 1 and FIG. 2, it is understood that the first wearable electronic device 11 is a mixed reality headset, and is configured to be worn on a head portion of the user 2. In the present invention, there are an image capturing unit 111, a head motion sensor unit 112, a first object recognizing unit HOR, a first circumstance recognizing unit HIS, and a head activity recognizing unit HHO provided in the first wearable electronic device 11.

As described in more detail below, the image capturing unit 111 is used for capturing a first image including at least one object and a work environment from a first person perspective of the user 2. Herein it needs to be further explained that the forgoing object is a necessary article for the user's work, such as a tool, a component, a material, an equipment, a machine, or an apparatus. On the other hand, the work environment may be an office place, a clean room or a factory provided with production line therein. In the present invention, the head motion sensor unit 112 includes at least one inertial sensor, and is used for achieving a head motion detection of the head portion, wherein the head motion detection is selected from the group consisting of rotation angle detection, rotation frequency detection, tilt angle detection, position detection, and a combination of the forgoing two or more detections. Moreover, the first object recognizing unit HOR is configured for generating a first object recognition data by applying an object recognizing process to the first image. On the other hand, the first circumstance recognizing unit HIS is configured for generating a work environment recognition data by applying a circumstance recognizing process to the first image, and the head activity recognizing unit HHO is configured for generating a head activity recognition data by applying a head activity recognizing process to a head motion sensing data that is transmitted from the head motion sensor unit 112.

Figure 4:
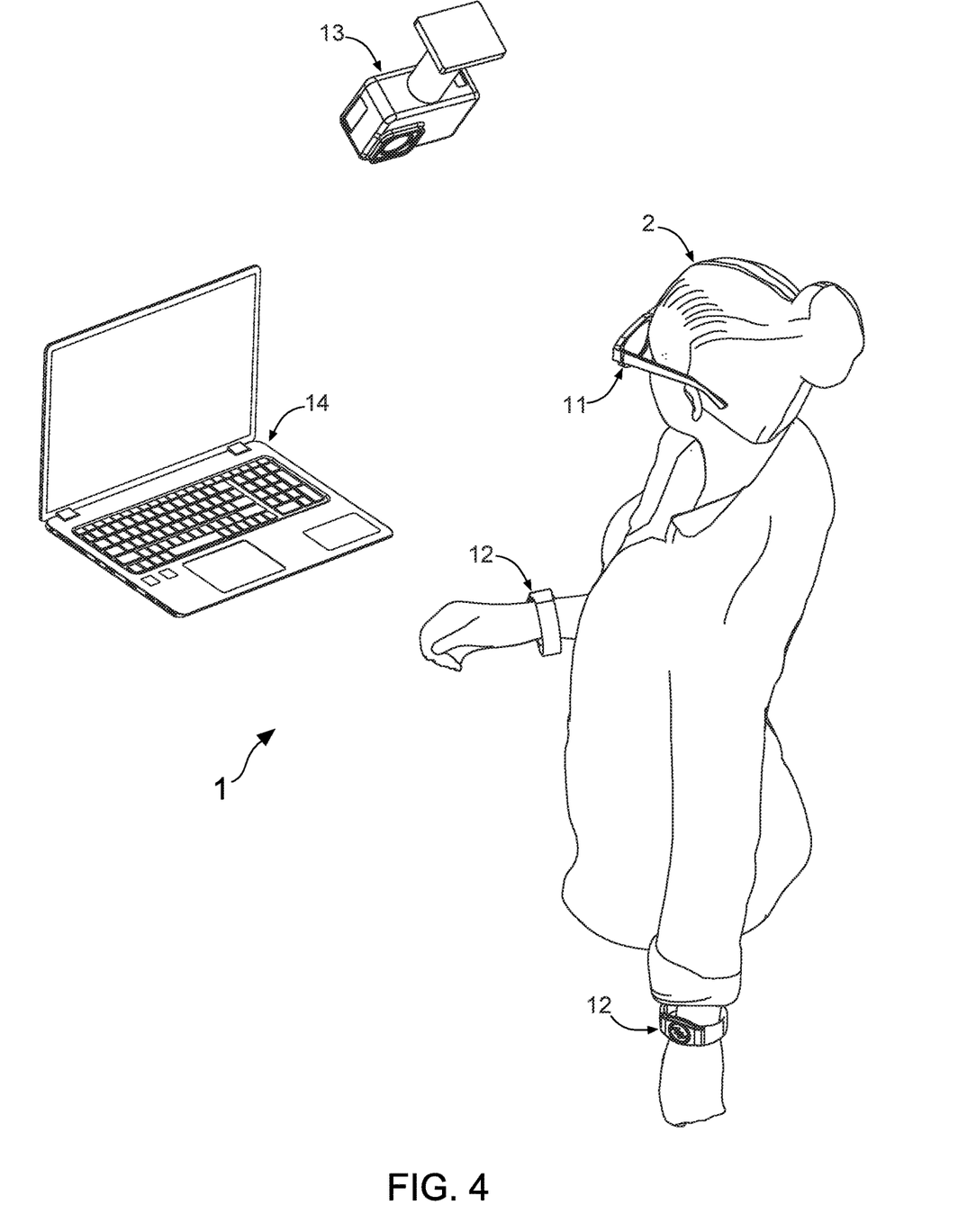
FIG. 4 shows a second diagram for describing a system for recognizing abnormal activity of human body of the present invention.

It is worth explaining that the first wearable electronic device 11 (like a MR headset) certainly has a microprocessor. In a practicable embodiment, the first object recognizing unit HOR, the first circumstance recognizing unit HIS and the head activity recognizing unit HHO are provided in the microprocessor of the first wearable electronic device 11 by a form of firmware, function library, application program, or operands. In addition, it needs to be particularly emphasized that the first wearable electronic device 11 is not certainly limited to be a MR headset that is shown in FIG. 1. In a practicable embodiment, the first wearable electronic device 11 can also be smart glasses that are shown in FIG. 4.

Figure 5:
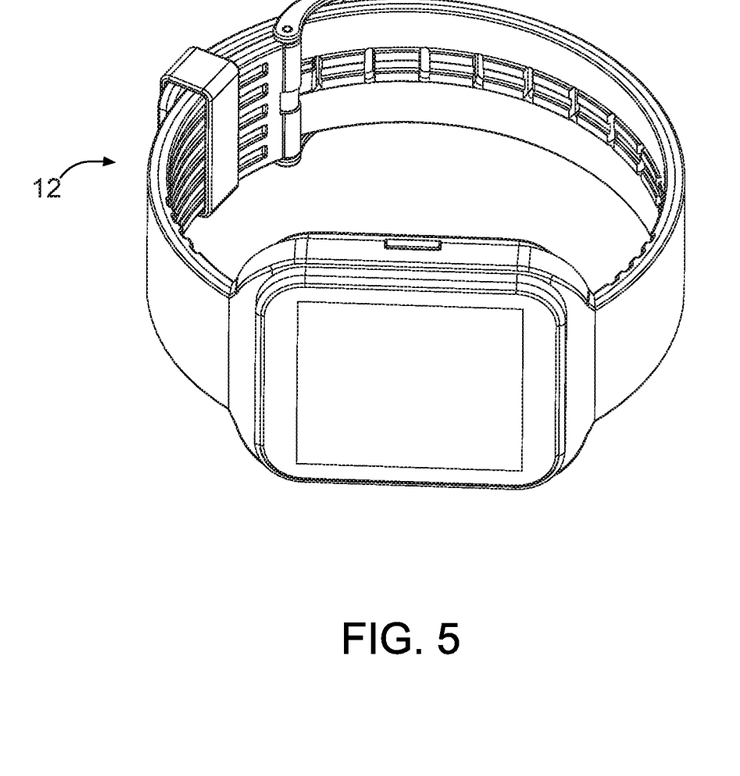
FIG. 5 shows a diagram for describing a different embodiment of the second wearable electronic device.

Please refer to FIG. 1 and FIG. 3 again. The plurality of second wearable electronic devices 12 are configured to be worn on two wrist portions of the user 2. According to the particular design of the present invention, the second wearable electronic device 12 is provided with a wrist motion sensor unit 121 and a wrist activity recognizing unit WGAR therein. The wrist motion sensor unit 121 is used for achieving a wrist motion detection of each of the two wrist portions, and the forgoing the wrist motion detection is selected from the group consisting of rotation angle detection, rotation frequency detection, tilt angle detection, position detection, and a combination of the forgoing two or more detections. Moreover, the wrist activity recognizing unit WGAR is configured for generating a wrist activity recognition data by applying a wrist activity recognizing process to a wrist motion sensing data that is transmitted from the wrist motion sensor unit 121. Herein, it is necessary to particularly emphasize that the second wearable electronic device 12 is not certainly limited to be a smart wristband that is shown in FIG. 1. In a practicable embodiment, the second wearable electronic device 12 can also be a smart watch that is shown in FIG. 5.

It should be known that the second wearable electronic device 12 (such as a smart wristband) certainly has a microprocessor. In a practicable embodiment, the wrist activity recognizing unit WGAR is also provided in the microprocessor of the second wearable electronic device 12 by a form of firmware, function library, application program, or operands. In addition, FIG. 1 and FIG. 3 also depict that the camera 13 is configured to capture a second image including the user 2, the at least one object and the work environment. Particularly, the present provides a body pose forecasting unit FPE, a second object recognizing unit FOR, and a second circumstance recognizing unit FIS in the camera 13. In which, the second object recognizing unit FOR is configured for generating a second object recognition data by applying the object recognizing process to the second image, and the second circumstance recognizing unit FIS is configured for generating a second circumstance recognition data by applying the circumstance recognizing process to the second image. It is worth mentioning that the body pose forecasting unit FPE is configured for generating a body pose forecast data according to at least one body pose feature that is extracted from the second image.

It should be known that the camera 13 also has a microprocessor, such that the second object recognizing unit FOR, the second circumstance recognizing unit FIS and the body pose forecasting unit FPE are provided in the microprocessor of the camera 13 by a form of firmware, function library, application program, or operands. As described in more detail below, the judgment module 14 is coupled to the first wearable electronic device 11, the plurality of wearable electronic devices 12 and the camera 13, and includes a data synchronization unit 140, a data fusion unit 141 and a judgment unit 142. In the judgment module 14, the data synchronization unit 140 is configured to transmit a data synchronization signal to the first wearable electronic device 11, the plurality of second wearable electronic devices 12, and the camera 13, such that the data fusion unit 141 simultaneously receives the first object recognition data, the first circumstance recognition data comprising the work environment recognition data and the head activity recognition data that are transmitted from the first wearable electronic device 11. Moreover, the data fusion unit 141 also simultaneously receives the second object recognition data, the second circumstance recognition data and the body pose forecast data that are transmitted from the camera 13. Furthermore, the data fusion unit 141 also simultaneously receives a wrist activity recognition data that is transmitted from second wearable electronic devices 13.

Consequently, the data fusion unit 141 generates a fusion data for being transmitted to the judgment unit 142, such that the judgment unit 142 coupled to the data fusion unit 141 is able to determine whether the user 2 is in an event of abnormal body activity or not, under referring the fusion data that is transmitted from the data fusion unit 141 and at least one reference data. Herein, FIG. 1 depicts that the judgment module 14 is a data processing device such as a laptop computer, wherein the data processing device includes a storage unit for storing the reference data that includes a document of standard operating procedures (SOP), an operating manual and a document of safety operation standard (SOS). On the other hand, in a practicable embodiment, the data fusion unit 141 and the judgment unit 142 are provided in the data processing device (i.e., the judgment module 14) by a form of firmware, function library, application program, or operands. Herein, it needs to particularly emphasize that, the judgment module 14 (i.e., data processing device) is not certainly limited to be a laptop computer that is shown in FIG. 1. In a practicable embodiment, the judgment module 14 can also be a central control system, an industrial computer, a server computer, a desk computer, a laptop computer, a tablet PC, and a smart phone.

Figure 6:
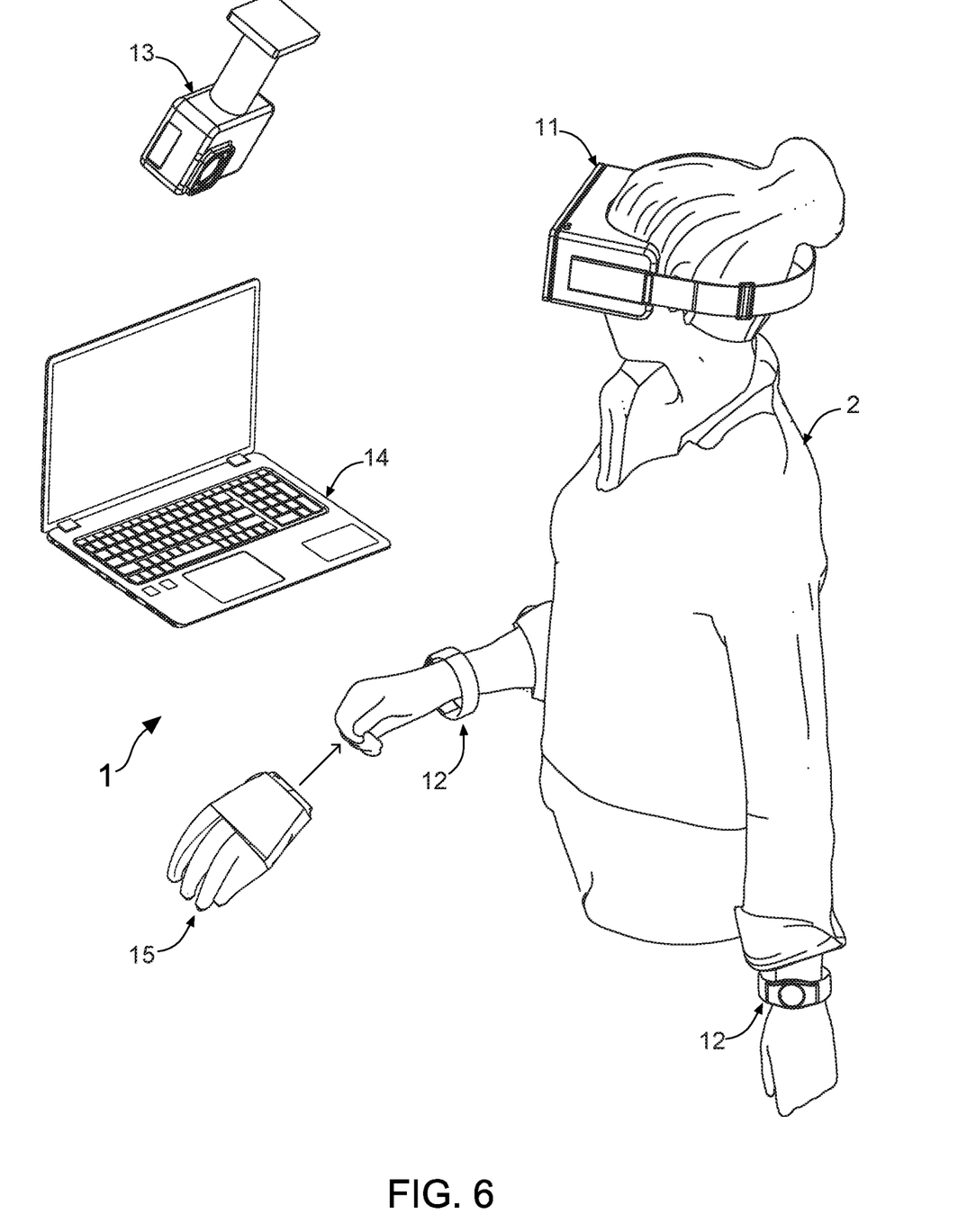
FIG. 6 shows a third diagram for describing a system for recognizing abnormal activity of human body of the present invention.
Figure 7:
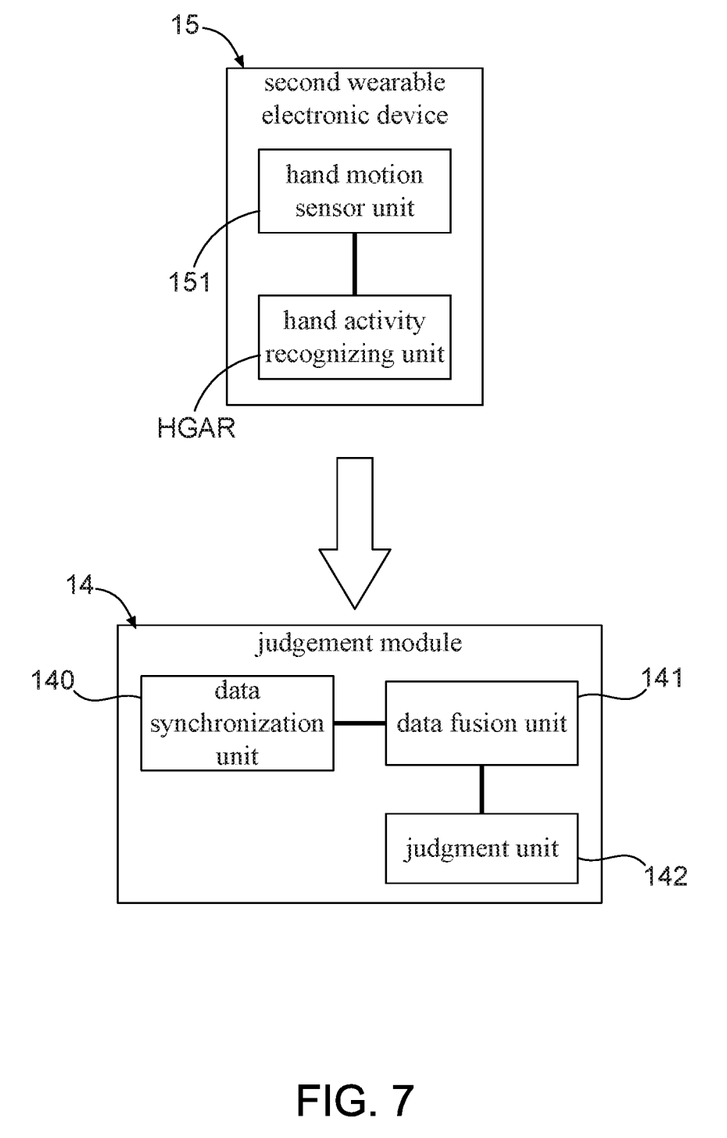
FIG. 7 shows a block diagram of a third wearable electronic device and the judgment module of the system for recognizing abnormal activity of human body.

FIG. 6 shows a third diagram for describing a system for recognizing abnormal activity of a human body of the present invention. After comparing FIG. 6 with FIG. 1, it is understood that the system 1 for recognizing abnormal activity of human body of the present invention that is shown in FIG. 6 further includes a third wearable electronic device 15. The third wearable electronic device 15 is coupled to the judgment module 14, and configured to be worn on a hand portion of the user 2. In one embodiment, the third wearable electronic device 15 is a smart glove, and FIG. 7 shows a block diagram of the third wearable electronic device 15 and the judgment module 14. Particularly, the present invention provides a hand motion sensor unit 151 and a hand activity recognizing unit HGAR in the third wearable electronic device 15. The hand motion sensor unit 151 is configured for achieving a hand motion detection of the hand portion of the user 2, and the hand activity recognizing unit HGAR is configured to generate a hand activity recognition data for the judgment module 14 by applying a hand activity recognizing process to a hand motion sensing data that is transmitted from the hand motion sensor unit 151.

In a practicable embodiment, the forgoing hand motion detection is selected from the group consisting of rotation angle detection, rotation frequency detection, tilt angle detection, position detection, detection of first clenching, detection of hand opening, finger activity detection, and a combination of the forgoing two or more detections. Moreover, it should be known that the data synchronization unit 140 of the judgment module 14 is also coupled to the third wearable electronic device 15, so as to transmit a data synchronization signal to the first wearable electronic device 11, the plurality of second wearable electronic devices 12, the camera 13, and the third wearable electronic device 15, such that the data fusion unit 141 simultaneously receives the first object recognition data, the first circumstance recognition data comprising the work environment recognition data and the head activity recognition data, the wrist activity recognition data, the second object recognition data, the second circumstance recognition data, the body pose forecast data, and the hand activity recognition data.

Therefore, through above descriptions, all embodiments and their constituting elements of the system for recognizing abnormal activity of human body proposed by the present invention have been introduced completely and clearly; in summary, the present invention includes the advantages of:

The present invention discloses a system 1 for recognizing abnormal activity of human body, including a first wearable electronic device 11, a plurality of second wearable electronic devices 12, at least one camera module 13, and a judgment module 14. This novel system 1 is suitable for application in any type of work environment, so as to monitor and determine whether a user 2 (i.e., an operator or an employee) exhibits abnormal activities by referring to a document of standard operating procedures (SOP), an operating manual and a document of safety operation standard (SOS), such that it facilitates a reduction in the rate of the user's mishandling, thereby achieving the enhancement of work efficiency and productivity.

As such, under the application of the system 1 for recognizing abnormal activity of human body proposed by the present invention, a staff of a back-end management system is able to immediately monitor each of the operators by using this system 1, thereby confirming each of the operators is performing his job and/or machine operation responsibly and meeting the requirements of the SOP document, the operating manual and the SOS document. On the other hand, this system 1 is also provided with a body pose forecasting function, such that it transmits a warning signal to the back-end management system in case of a next body pose of the operator being forecasted to be an abnormal human activity. As a result, the staff of the back-end management system is able to inform the operator to fix his body pose in advance, thereby effectively avoiding the workplace incident from occurring due to the operator's mishandling.

The above description is made on embodiments of the present invention. However, the embodiments are not intended to limit scope of the present invention, and all equivalent implementations or alterations within the spirit of the present invention still fall within the scope of the present invention.

What is claimed is:

1. A system for recognizing abnormal activity of human body, comprising:
    a first wearable electronic device, being configured to be worn on a head portion of a user, and having an image capturing unit and a head motion sensor unit, wherein the image capturing unit is used for capturing a first image including at least one object and a work environment, and the head motion sensor unit being used for achieving a head motion detection of the head portion;
    a plurality of second wearable electronic devices, being configured to be worn on two wrist portions of the user, and having a wrist motion sensor unit for achieving a wrist motion detection of each of the two wrist portions;
    at least one camera, being configured to capture a second image including the user, the at least one object and the work environment, and having a body pose forecasting unit for generating a body pose forecast data according to at least one body pose feature that is extracted from the second image;
    a judgment module, coupled to the first wearable electronic device, the plurality of wearable electronic devices and the camera, and comprising:
        a data fusion unit, being configured to receive a first object recognition data, a first circumstance recognition data comprising a head activity recognition data and a work environment recognition data that are transmitted from the first wearable electronic device, a wrist activity recognition data that is transmitted from second wearable electronic devices, and a second object recognition data, a second circumstance recognition data and the body pose forecast data that are transmitted from the camera, thereby generating a fusion data; and
        a judgment unit, coupled to the data fusion unit, and configured to determine whether the user is in an event of abnormal body activity based upon the fusion data and at least one reference data.

2. The system of claim 1, wherein the first wearable electronic device is selected from the group consisting of a mixed reality headset and smart glasses.

3. The system of claim 1, wherein the second wearable electronic device is selected from the group consisting of a smart wristband and a smart watch.

4. The system of claim 1, wherein the judgment module is a data processing device, and the data fusion unit and the judgment unit are provided in the data processing device by a form of firmware, function library, application program, or operands.

5. The system of claim 4, wherein the data processing device is selected from the group consisting of a central control system, industrial computer, server computer, desk computer, laptop computer, tablet PC, and smart phone.

6. The system of claim 1, wherein the judgement module further comprises a storage unit for storing the reference data that comprises a document of standard operating procedures (SOP), an operating manual and a document of safety operation standard (SOS).

7. The system of claim 1, wherein the head motion sensor unit and the wrist motion sensor unit each comprise at least one inertial sensor.

8. The system of claim 1, wherein the first wearable electronic device further comprises:
a first object recognizing unit, being configured for generating the first object recognition data by applying an object recognizing process to the first image;
a first circumstance recognizing unit, being configured for generating the work environment recognition data by applying a circumstance recognizing process to the first image; and
a head activity recognizing unit, configured for generating a head activity recognition data by applying a head activity recognizing process to a head motion sensing data that is transmitted from the head motion sensor unit, wherein the first object recognizing unit, the first circumstance recognizing unit and the head activity recognizing unit are provided in a microprocessor of the first wearable electronic device by a form of firmware, function library, application program, or operands.

9. The system of claim 8, wherein the camera comprises:
a second object recognizing unit, configured for generating the second object recognition data by applying the object recognizing process to the second image;
a second circumstance recognizing unit, configured for generating the second circumstance recognition data by applying the circumstance recognizing process to the second image; and
a head activity recognizing unit, configured for generating a head activity recognition data by applying a head activity recognizing process to a head motion sensing data that is transmitted from the head motion sensor unit.

10. The system of claim 9, wherein the second object recognizing unit, the second circumstance recognizing unit, and the body pose forecasting unit are provided in a microprocessor of the camera by a form of firmware, function library, application program, or operands.

11. The system of claim 1, wherein the second wearable electronic device further comprises:
a wrist activity recognizing unit, being configured for generating the wrist activity recognition data by applying a wrist activity recognizing process to a wrist motion sensing data that is transmitted from the wrist motion sensor unit, wherein the wrist activity recognizing unit is provided in a microprocessor of the second wearable electronic device by a form of firmware, function library, application program, or operands.

12. The system of claim 1, wherein the head motion detection is selected from the group consisting of rotation angle detection, rotation frequency detection, tilt angle detection, position detection, and a combination of the forgoing two or more detections.

13. The system of claim 1, wherein the wrist motion detection is selected from the group consisting of rotation angle detection, rotation frequency detection, tilt angle detection, position detection, and a combination of the forgoing two or more detections.

14. The system of claim 1, further comprises a third wearable electronic device that is coupled to the judgment module, configured to be worn on a hand portion of the user, and comprising:
a hand motion sensor unit for achieving a hand motion detection of the hand portion of the user; and
a hand activity recognizing unit, configured for generating a hand activity recognition data for the judgment module by applying a hand activity recognizing process to a hand motion sensing data that is transmitted from the hand motion sensor unit.

15. The system of claim 14, wherein the hand motion detection is selected from the group consisting of rotation angle detection, rotation frequency detection, tilt angle detection, position detection, detection of first clenching, detection of hand opening, finger activity detection, and a combination of two or more of the foregoing detections.

16. The system of claim 15, wherein the judgment module further comprises a data synchronization unit, coupled to the first wearable electronic device, the plurality of second wearable electronic devices, the camera, and the third wearable electronic device, configured to transmit a data synchronization signal to the first wearable electronic device, the plurality of second wearable electronic devices, the camera, and the third wearable electronic device, wherein the data fusion unit simultaneously receives the first object recognition data, the first circumstance recognition data comprising the work environment recognition data and the head activity recognition data, the wrist activity recognition data, the second object recognition data, the second circumstance recognition data, the body pose forecast data, and the hand activity recognition data.

17. The system of claim 14, wherein the third wearable electronic device is a smart glove.

* * * * *